(12) United States Patent
Wolff (10) Patent No.: US 11,246,983 B2
(45) Date of Patent: Feb. 15, 2022

(54) INFUSION DEVICE AND METHOD FOR ADMINISTERING A MEDICAL FLUID TO A PATIENT

(71) Applicant: FRESENIUS VIAL SAS, Brezins (FR)

(72) Inventor: Remy Wolff, Morette (FR)

(73) Assignee: Fresenius Vial SAS, Brézins (FR)

( * ) Notice: Subject to any disclaimer, the term of this patent is extended or adjusted under 35 U.S.C. 154(b) by 372 days.

(21) Appl. No.: 15/751,376

(22) PCT Filed: Jul. 6, 2016

(86) PCT No.: PCT/EP2016/065959
§ 371 (c)(1),
(2) Date: Feb. 8, 2018

(87) PCT Pub. No.: WO2017/032498
PCT Pub. Date: Mar. 2, 2017

(65) Prior Publication Data
US 2018/0221575 A1    Aug. 9, 2018

(30) Foreign Application Priority Data

Aug. 24, 2015 (EP) .................... 15306306

(51) Int. Cl.
*A61M 5/168* (2006.01)
*A61M 5/142* (2006.01)
*A61M 5/145* (2006.01)

(52) U.S. Cl.
CPC ........ *A61M 5/16854* (2013.01); *A61M 5/145* (2013.01); *A61M 5/14212* (2013.01);
(Continued)

(58) Field of Classification Search
CPC .......... A61M 5/16854; A61M 5/16831; A61M 5/168; A61M 5/14; A61M 5/145;
(Continued)

(56) References Cited

U.S. PATENT DOCUMENTS

2007/0191770 A1    8/2007 Moberg et al.
2009/0177148 A1    7/2009 Delcastilio et al.
(Continued)

FOREIGN PATENT DOCUMENTS

CN    103977479    8/2014

OTHER PUBLICATIONS

International Search Report and Written Opinion, counterpart PCT Appl. No. PCT/EP2016/065959, 14 pages (dated Oct. 5, 2016).

*Primary Examiner* — Kevin C Sirmons
*Assistant Examiner* — Alexandra Lalonde
(74) *Attorney, Agent, or Firm* — Cook Alex Ltd.

(57) ABSTRACT

An infusion device includes a pump for pumping a medical fluid from a fluid container through a delivery line towards a patient at a flow rate, a sensor for measuring a force on the pump or the delivery line, and a processor device configured to derive, from the force measured by the sensor, a pressure value indicative of the pressure in the delivery line and to compare the pressure value to a threshold value for determining whether an occlusion in the delivery line is present. A storage device stores a compliance value associated with the pump and/or the delivery line, and the processor device is configured to compute, from the stored compliance value, the flow rate and the threshold value, an estimate of a duration between the time of an occurrence of an occlusion and the time at which the pressure value exceeds the threshold value.

9 Claims, 3 Drawing Sheets

(52) U.S. Cl.
CPC . *A61M 5/1452* (2013.01); *A61M 2005/16863* (2013.01); *A61M 2005/16872* (2013.01); *A61M 2205/18* (2013.01); *A61M 2205/332* (2013.01); *A61M 2205/505* (2013.01); *A61M 2205/52* (2013.01)

(58) Field of Classification Search
CPC ......... A61M 2005/16872; A61M 2005/16868; A61M 2005/16863; A61M 2205/18; A61M 2205/3334; A61M 2205/50; A61M 2205/52; A61M 2205/3355; A61M 2205/505; A61M 2205/332
See application file for complete search history.

(56) References Cited

U.S. PATENT DOCUMENTS

| | | | |
|---|---|---|---|
| 2010/0121170 A1* | 5/2010 | Rule | A61B 5/14532 600/365 |
| 2011/0224523 A1* | 9/2011 | Budiman | A61B 5/14532 600/365 |
| 2011/0270058 A1* | 11/2011 | Price | A61B 5/021 600/324 |
| 2012/0123229 A1* | 5/2012 | Butterfield | A61M 5/16854 600/309 |
| 2012/0283691 A1* | 11/2012 | Barnes | A61M 5/00 604/500 |
| 2014/0288947 A1* | 9/2014 | Simpson | G16H 20/40 705/2 |
| 2016/0361492 A1* | 12/2016 | Nunez | A61M 16/0003 |

\* cited by examiner

INFUSION DEVICE AND METHOD FOR ADMINISTERING A MEDICAL FLUID TO A PATIENT

The present application is a U.S. National Stage of PCT International Patent Application No. PCT/EP2016/065959, filed Jul. 6, 2016, which claims priority to EP Application No. 15306306, filed Aug. 24, 2015, both of which are hereby incorporated herein by reference.

The invention relates to an infusion device for administering a medical fluid to a patient according to the preamble of claim 1 and to a method for administering a medical fluid to a patient.

An infusion device of this kind comprises a pumping mechanism for pumping a medical fluid from a fluid container through a delivery line towards a patient at a set flow rate, a sensor device for measuring a force on the pumping mechanism or on the delivery line, and a processor device for deriving, from the force measured by the sensor device, a pressure value indicative of the pressure in the delivery line. Herein, the processor device is constituted to compare the pressure value to a threshold value for determining whether an occlusion in the delivery line is present or not.

An infusion device of this kind may for example be constituted as a syringe pump or as a peristaltic (volumetric) infusion pump. Within a syringe pump, a medical fluid (such as a medication or a nutritional fluid for example for the parenteral feeding of a patient) is contained in a cylindrical tube of a syringe. By continuously pushing a plunger of the syringe into the cylindrical tube the medical fluid is delivered out of the cylindrical tube through a suitable delivery line towards a patient for infusing the medical fluid into the patient.

Within a syringe pump, a force sensor is for example placed on a driving element of the pumping mechanism of the infusion device acting onto the plunger of the syringe. By measuring the force exerted on the plunger the pressure within the cylindrical tube of the syringe (which is connected downstream to the delivery line) can be derived. Generally herein, the pressure within the cylindrical tube during a normal infusion process can be assumed to be (almost) 0, due to the resistance for delivering the medical fluid towards the patient being small. However, if an occlusion is present in the delivery line downstream of the cylindrical tube of the syringe, the pressure in the cylindrical tube will rise, which can be detected via the force sensor and which can be used to trigger an alarm if the pressure exceeds a certain preset threshold value.

The pressure threshold value used for the occlusion detection can for example be programmed by a user prior to conducting an infusion operation. Herein the user may enter a desired threshold value during the initial programming of the device, and this threshold value is then used during operation for determining whether an occlusion is present or not.

In this regard, however, the user must be aware of the fact that generally an alarm will not be triggered immediately upon occurrence of an occlusion. Rather, the pressure measured on the pumping mechanism or on the delivery line will rise continuously and will reach the threshold value only sometime after the actual occurrence of the occlusion. The time between reaching the threshold and the actual occurrence of the occlusion depends for example on the flow rate, the set threshold value and the mechanical characteristics of the pumping mechanism or the tubing set used together with the pumping mechanism. An alarm hence is triggered only after a substantial time has passed following the occurrence of an occlusion, for example 30 minutes, an hour or even more after the occlusion first occurred. If a continuous infusion of a medical fluid into a patient at a constant dose rate is required, a prolonged interruption of the infusion process may pose a severe problem and potentially may be hazardous to the patient.

Generally, in the instructions for use distributed with an infusion device it is stated, for example in a table, what time may pass between the occurrence of an occlusion and the actual triggering of an alarm. This approach however has drawbacks, because a user generally will not refer to the instructions for use prior to each infusion operation, and the instructions for use generally will list estimated time delays only for certain situations, for example for specific tubing sets at specific flowrates, but cannot cover all different scenarios and may not allow a user to easily derive an estimate for a specific situation not explicitly included in the description.

A user, for example a nurse, hence may have a rather low confidence in the triggering of an occlusion alarm, which may cause the user to check on the infusion device more often than actually necessary, putting an additional burden on the user, for example a nurse, which already is faced with a great variety of different tasks for example in a hospital environment, for example in an intensive care unit of a hospital.

It is an object of the instant invention to provide an infusion device and a method for administering a medical fluid to a patient which may facilitate the programming of a threshold value for the occlusion detection and may provide a higher level of confidence to a user for the occlusion detection.

This object is achieved by means of an infusion device comprising the features of claim 1.

Herein, the infusion device comprises a storage device storing a compliance value associated with the pumping mechanism and/or the delivery line, wherein the processor device is constituted to compute, from the stored compliance value, the flow rate and the threshold value, an estimate of a duration between the time of an occurrence of an occlusion in the delivery line and the time at which the pressure value exceeds the threshold value.

The processor device hence is constituted to compute an estimate of a duration indicating the time span between the time of the actual occurrence of an occlusion and the time at which the derived pressure value exceeds the threshold value such that an alarm may be triggered. This estimate of the duration may for example be displayed to a user, such that a user, when she for example enters a threshold value into the infusion device, immediately obtains a feedback about the time duration that (approximately) may pass between the actual occurrence of an occlusion and the time at which finally an alarm is triggered.

If the user in this way for example obtains the information that the time span between the occurrence of the occlusion and the alarm may be for example an hour or even longer, the user may adapt the threshold value such that a shorter time duration, for example 15 minutes, is obtained. The feedback hence allows the user to suitably adjust the programming of the threshold value.

For computing the estimate of the duration, the processor device takes into account the flow rate, the threshold value and a compliance value associated with the pumping mechanism and/or the delivery line. The compliance value in this regard is to be understood as a measure for the expansibility of the system, for example a cylindrical tube of a syringe used on the syringe pump or a delivery line extending between the pumping mechanism and the patient. Generally, the compliance indicates the change of volume per pressure and accordingly is stated for example in ml/bar. With respect to for example a tubing set, the compliance indicates by what volume a tube expands if the pressure increases by a certain margin.

The compliance for a system can be measured easily by subjecting a system, for example a tube set, to pressure and measure the change in volume.

The instant invention makes use of the finding that the rise of pressure within the system also depends on the compliance of the system. A large compliance will lead to a slower rise in pressure (because the system, for example a tubing set, expands when the pressure rises), whereas a small compliance will lead to a fast rise in pressure.

The infusion device hence stores, in its storage device, a compliance value associated with the pumping mechanism and/or the delivery line, wherein part of the pumping mechanism may for example be a syringe whose plunger is moved for delivering a medical fluid out of a cylindrical tube of the syringe through the delivery line towards a patient. The compliance value may be a constant value. It however is also conceivable that the compliance value depends on the pressure and hence non-linearly changes with the pressure.

The infusion device may for example comprise an input device allowing a user to program the flow rate and/or the threshold value. The input device may for example be constituted by a touch-sensitive display, via which the user may enter the flow rate at which the infusion process shall be carried out and the threshold value which shall be used for the occlusion detection. Upon programming of the flow rate and/or the threshold value the processor device may immediately compute the estimate of the duration between the time of an occurrence of an occlusion in the delivery line and the time at which the pressure value exceeds the threshold value, such that the user obtains an immediate feedback and may suitably adjust for example the threshold value such that the time duration falls into an acceptable range.

The storage device may for example store a multiplicity of compliance values associated with a multiplicity of different pumping mechanisms and/or delivery lines. By entering into the infusion device what pumping mechanism, for example what type of syringe, and what delivery line, for example what tubing set, is used, the processor device may obtain the associated compliance value from the storage device and may use this compliance value for its computations.

If a particular type of syringe is not defined within the storage device, for example a default value may be used. If for example a syringe is used of a particular manufacturer having a predefined volume, for example 50 ml, a default value for a 50 ml syringe may be used if the particular syringe from the particular manufacturer is not known to the system.

As said, the compliance value may be a constant or may be defined by a (non-linear) relation depending on the pressure.

The processor device may for example be constituted to compute the estimate of the duration making use of the following equation:

$$T = \frac{P_{thres} \cdot C}{f},$$

Herein, T represents the duration between the time of occurrence of an occlusion in the delivery line and the time at which the pressure value exceeds the threshold value, $P_{thres}$ represents the threshold value, and f represents the flow rate.

The infusion device may for example be constituted as a syringe pump. In this case the pumping mechanism may be constituted by the mechanical system of the infusion pump in combination with the particular syringe. For example, the syringe comprises a cylindrical tube and a plunger movable in the cylindrical tube, wherein the pumping mechanism of the infusion pump comprises a driving element acting onto the plunger for continuously moving the plunger into the cylindrical tube in order to deliver a medical fluid from the cylindrical tube towards a patient. The storage device in this case beneficially stores a compliance value associated with the particular syringe (or a similar syringe having comparable mechanical characteristics) used on the syringe pump.

In an alternative embodiment the infusion device may be constituted as a volumetric (peristaltic) pump, wherein the storage device stores a compliance value of a tubing set used on the volumetric pump. In this case the pumping mechanism may for example comprise a wobbling device acting onto a pump module of a disposable tubing set for pumping a medical fluid through the pump module in a peristaltic fashion.

The infusion device, in one embodiment, comprises a display device constituted to display the computed estimate of the duration. Herein, the display device may for example be a touch-sensitive display allowing a user to input commands as well as displaying information such as operational parameters.

In one embodiment the processor device may be constituted to issue a warning if the computed estimate of the duration exceeds a predetermined limit. Hence, upon entering a threshold value, a user is immediately warned if the estimated duration between the occurrence of an occlusion and the time of the triggering of an alarm becomes too large. For example, a user may be prevented from entering a threshold value which leads to an excessive estimate of duration between the occurrence of the occlusion and the time of triggering an alarm, for example by prompting the user to enter another, smaller threshold value.

In another embodiment the processor device may be constituted to compute a threshold value such that an estimate of a duration between the time of occurrence of an occlusion in the delivery line and the time at which the pressure value exceeds the threshold value is obtained which falls into a predefined range. In this case, hence, the setting of the threshold value may take place automatically without interaction by a user, wherein the processor device may set the threshold value such that a desirable duration between the time of occurrence of an occlusion and the actual triggering of an alarm is obtained.

The predefined range may for example have an upper bound of 30 minutes, preferably 15 minutes, even more preferably 10 minutes. The lower bound may for example be at 5 minutes. Generally the threshold value should not be chosen too small in order to avoid false alarms, but should also not be chosen too large in order to avoid long time durations between the actual occurrence of the occlusion and the time of triggering an alarm.

The object is also achieved by a method using an infusion device for administering a medical fluid to a patient, in which:

a pumping mechanism pumps a medical fluid from a fluid container through a delivery line towards a patient at a set flow rate, a sensor device measures a force on the pumping mechanism or the delivery line, and a processor device derives, from the force measured by the sensor device, a pressure value indicative of the pressure in the delivery line, wherein the processor device is constituted to compare the pressure value to a threshold value for determining whether an occlusion in the delivery line is present or not.

Herein, a storage device stores a compliance value associated with the pumping mechanism and/or the delivery line, wherein the processor device computes, from the stored compliance value, the flow rate and the threshold value, an estimate of a duration between the time of an occurrence of an occlusion in the delivery line and the time at which the pressure value exceeds the threshold value.

The advantages and advantageous embodiments described above for the infusion device equally apply also to the method, such that it shall be referred to the above.

The computing of the estimate of the duration between the time of an occurrence of an occlusion in the delivery line and the time at which the pressure value exceeds the threshold value beneficially takes place upon the programming of the infusion device by a user and hence prior to the actual operation of the infusion device.

The idea of the invention shall subsequently be described in more detail with reference to the embodiments shown in the figures. Herein.

Figure 1:
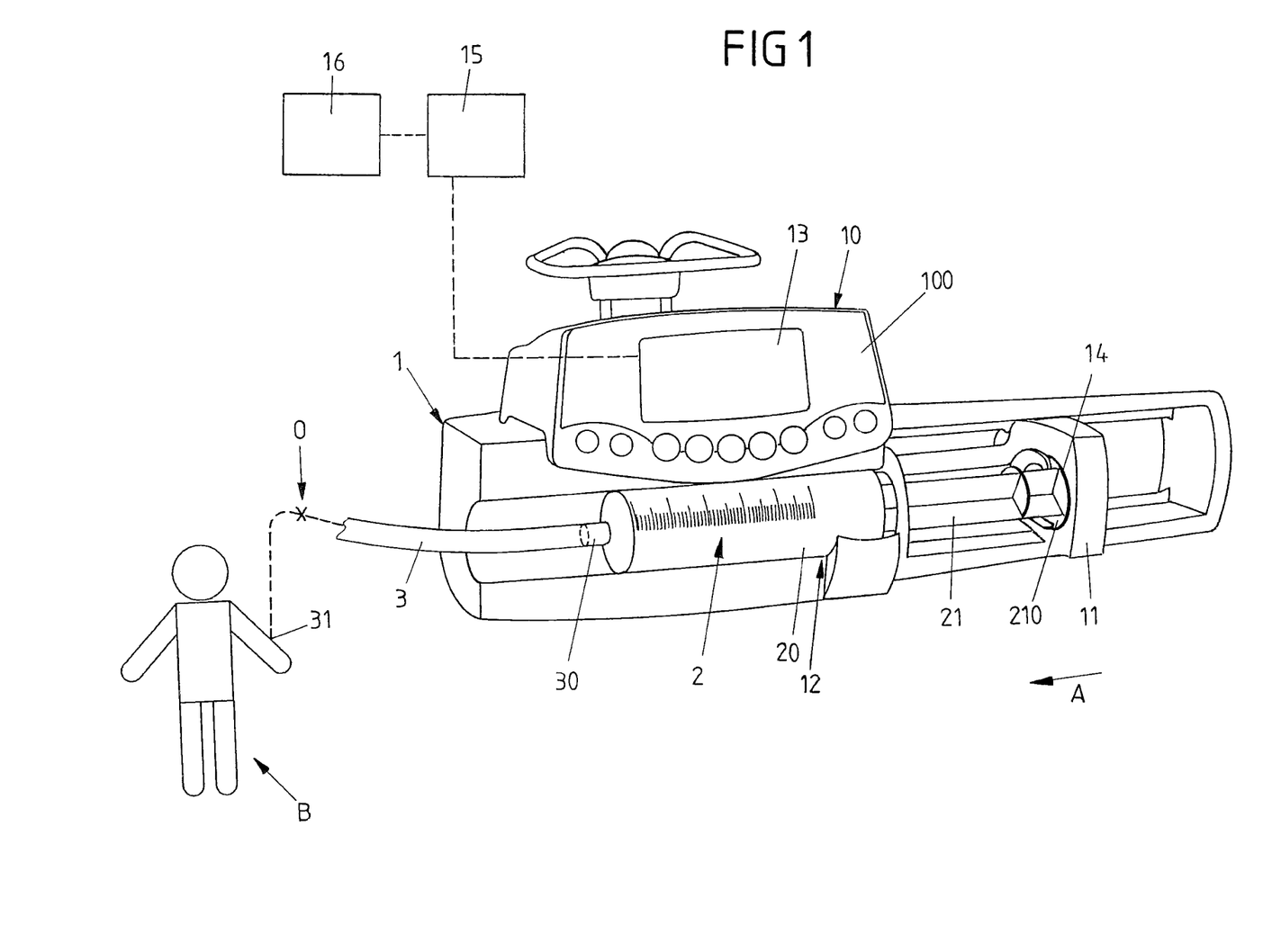
FIG. 1 shows a view of an infusion device constituted as a syringe pump.

FIG. 1 shows an embodiment of an infusion device 1 in the shape of a syringe pump. The infusion device 1 comprises a housing 10 having a front face 100 and a display device 13 arranged thereon. The display device 13 may for example be a touch-sensitive display allowing a user to enter commands for operation of the infusion device 1 and displaying operational information regarding the process of an actual infusion operation.

The infusion device 1 comprises a receptacle 12 in which a syringe 2 having a cylindrical tube 20 is arranged. A plunger 21 is movable within the cylindrical tube 20 and is in engagement with a driving element 11 of a pumping mechanism of the infusion device 1. At an end of the cylindrical tube 20 opposite the plunger 21 a delivery line 3 extends from the cylindrical tube 20 towards a patient B, the delivery line 3 being connected to the cylindrical tube 20 at an end 30 and to the patient B at an end 31.

The plunger 21 comprises a head 210 facing away from the cylindrical tube 20 and being in abutment with the driving element 11 of the infusion device 1. During operation of the infusion device 1, the driving element 11 is electromotorically driven in an actuation direction A such that the plunger 21 is moved into the cylindrical tube 20 and a medical fluid contained in the cylindrical tube 20 is delivered via the delivery line 3 towards the patient B.

The infusion device 1 comprises a processor device 15 and a storage device 16. Via the processor device 15 the infusion operation of the infusion device 1 is controlled. In the storage device 16 operational parameters, such as mechanical characteristics of the syringe 2 used on the infusion device 1 as well as operational data, may be stored.

During an infusion process a medical fluid, for example a medication or a nutritional fluid for the parenteral feeding of a patient or the like, is delivered from the cylindrical tube 20 via the delivery line 3 towards the patient B. For this, the plunger 21 is continuously pushed into the cylindrical tube 20 such that a desired flow rate is obtained, which is programmed by a user prior to the start of the infusion operation.

The delivery line 3 generally is made of a flexible tubing made for example from a PVC material. The delivery line extends from the cylindrical tube 20 to the patient B and is, at its first end 30, in fluid connection with the cylindrical tube 20 and, at its second end 31, for example connected to a needle for providing an intravenous access to the patient B. During an infusion process an occlusion O in the delivery line 3 must be avoided and, if it nevertheless occurs, must be detected such that appropriate countermeasures to overcome the occlusion O can be taken. For this, a force sensor 14 is placed on the driving element 11 facing the head 210 of the plunger 214 measuring a force exerted on the plunger 21 during an infusion process. From a force measured by means of the force sensor 14 an estimate of the pressure within the syringe 2 can be obtained, such that the pressure within the syringe 2 and the delivery line 3 can be monitored. If it is found that the pressure within the syringe 2 and the delivery line 3 rises beyond a permissible threshold value, an alarm is triggered indicating that an occlusion O may be present in the system.

Figure 2:
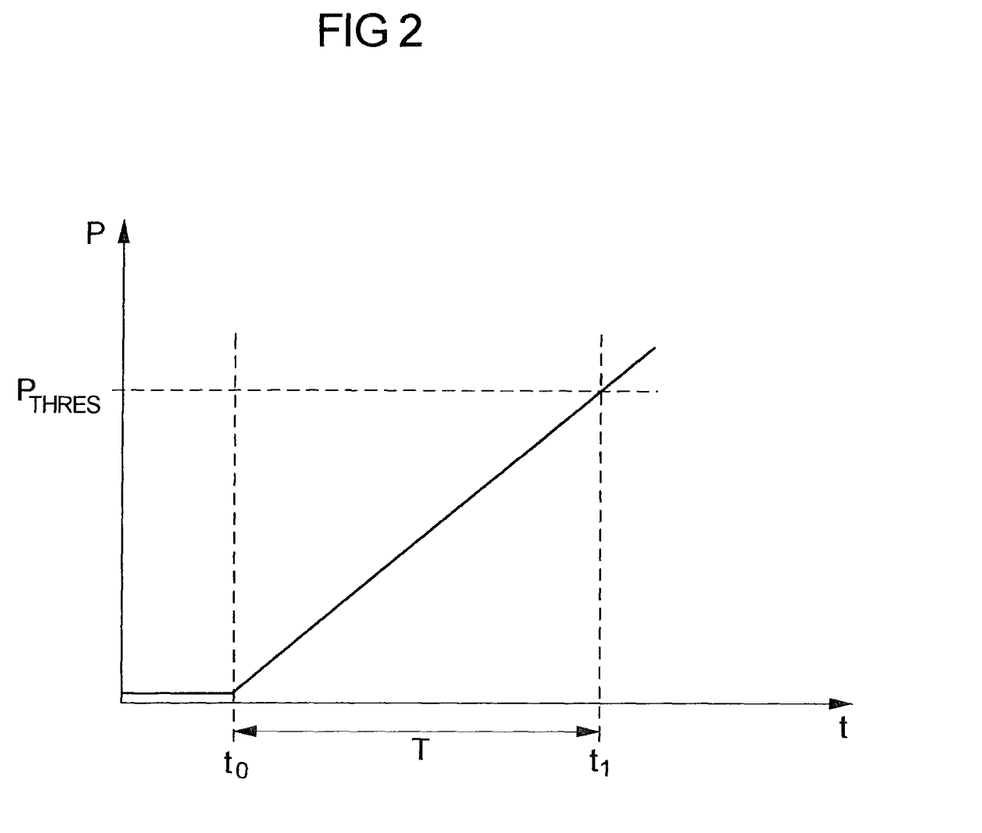
FIG. 2 shows a schematic diagram of a pressure rise over time in case of an occlusion.

FIG. 2 shows in a schematic diagram the pressure P over time t in case of an occlusion O. Generally, the pressure P is very small (almost 0) during normal infusion operation in case no occlusion O is present (see the pressure P prior to the time t0). If at the time t0 an occlusion O occurs, the pressure P will start to rise and will continue to rise (if the occlusion O does not disappear) until a threshold value $P_{thres}$ is exceeded, at which moment an alarm is triggered by the processor device 15 such that a user is warned of the occlusion O.

The occlusion O, in the example of FIG. 2, occurs at time t0. Until the pressure threshold value $P_{thres}$ actually is exceeded by the pressure curve P at time t1, a substantial time duration T may pass, due to the continuous rise of the pressure P following the occlusion O at a finite slope, the slope of the pressure rise herein depending on a multiplicity of factors, for example the flow rate and the compliance of the system, in particular the compliance of the cylindrical tube 20 of the syringe 2 and of the delivery line 3 extending in between the cylindrical tube 20 and the patient B.

Generally, the pressure in the delivery line 3 will rise according to the following equation:

$$P = \frac{f \cdot t}{C}.$$

Herein, P denotes the pressure, f denotes the flow rate, t denotes the time, and C denotes the compliance.

The time duration T also depends on the threshold value $P_{thres}$ such that by suitably setting the threshold value $P_{thres}$ the time duration T in between the occurrence of the occlusion O and the time of the alarm can be influenced. The preset threshold value $P_{thres}$ is for example programmed by a user prior to conducting an infusion process and should be chosen by the user such that the time duration T does not become excessively large (generally, the warning for an occlusion should be triggered in a timely fashion after occurrence of the occlusion O such that the infusion process is not interrupted for too long a time).

To facilitate the setting of the threshold value $P_{thres}$ for a user, the processor device 15 is constituted to compute an estimate of the time duration T making use of the following equation:

$$T = \frac{P_{thres} \cdot C}{f},$$

Herein, $P_{thres}$ denotes the threshold value, C denotes the compliance and f denotes the flow rate. Upon programming the threshold value $P_{thres}$ by a user, the processor device 15 immediately computes the estimate of the duration T and outputs the estimate to the user such that the user obtains a feedback about an estimate of the expected time in between the actual occurrence of an occlusion and the time at which an alarm the triggered during the actual infusion operation of the infusion device 1.

The compliance value C associated with the syringe 2 and the delivery line 3 is stored in the storage device 16 of the infusion device 1. The storage device 16 in this regard may store a multiplicity of compliance values C for different syringes 2 and different delivery lines 3 such that, by inputting for example the type of syringe 2 to the infusion device 1, the processor device 15 may refer to the compliance value C associated with the particular syringe 2 used on the system for computing the estimate of the duration T.

The storage device 16 may for example store a compliance value for a syringe 2 of a particular manufacturer and a particular volume. The storage device 16 may in addition store a default value for a syringe 2 of a particular volume, which may be used in case a particular syringe 2 of a particular manufacturer is not explicitly defined in the infusion device 1. A delivery line 3 may be identified by its length, its inner and/or outer diameter or the like and by its manufacturer, and associated with a particular type of delivery line 3 a particular compliance value may be stored in the storage device 16.

The storage device 16 may store a constant value for the compliance. Just as well it is conceivable that the storage device 6 stores a nonlinear relation for the compliance depending for example on the pressure in the system.

The computation of the estimate of the duration T may be used to provide a feedback to the user upon programming the threshold value $P_{thres}$. If the threshold value $P_{thres}$ exceeds a predetermined limit, for example 30 minutes, in addition a warning may be triggered to the user, or the user may be prevented from entering a threshold value $P_{thres}$ which causes the duration T to rise beyond the predefined limit.

Alternatively, the infusion device 1 may be constituted to set the threshold value $P_{thres}$ automatically such that the threshold value $P_{thres}$ falls within a predefined range. For example, upon programming the flow rate the system may set the threshold value $P_{thres}$ automatically such that the threshold value $P_{thres}$ is below for example 15 minutes and above for example 5 minutes.

The invention is not limited to syringe pumps as shown in FIG. 1. Rather, as illustrated in FIG. 3, the invention likewise is applicable also to volumetric pumps.

Figure 3:
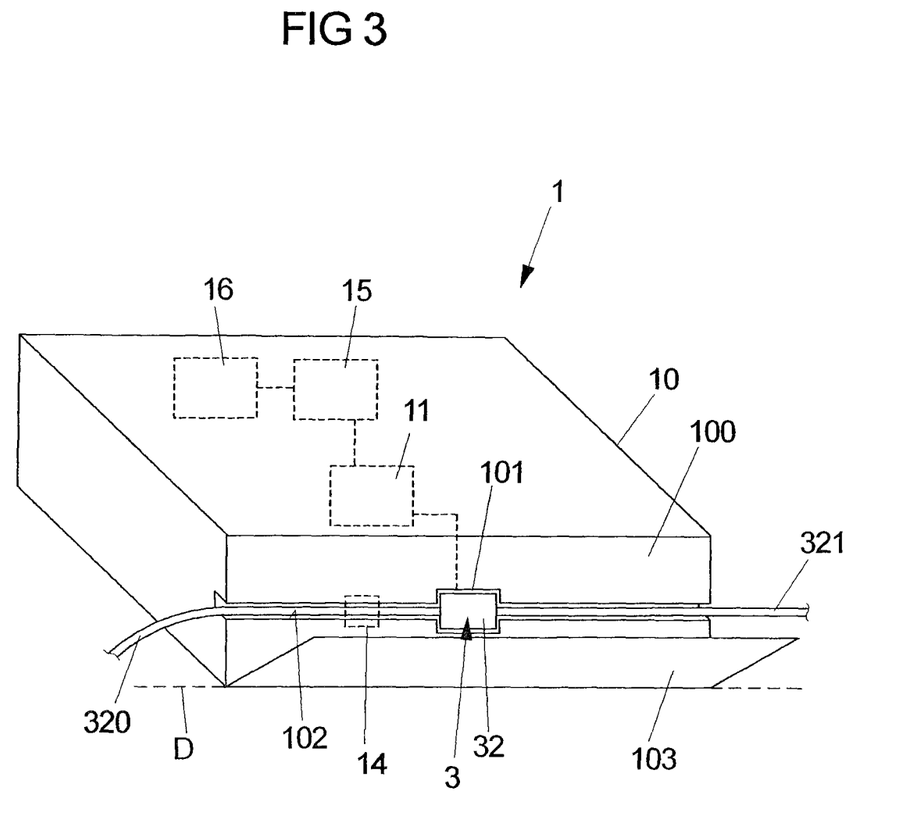
FIG. 3 shows a view of an infusion device in the shape of a volumetric (peristaltic) infusion pump.

In the example of FIG. 3, an infusion device 1 is constituted as a volumetric (peristaltic) infusion pump having a housing 10 and a front face 100 comprising a receptacle 101 in which a pump module 32 of an infusion set 3 can be received. A housing element 103 (also denoted as the "door") is pivotable about a pivoting axis D relative to the housing 10 and can be approached towards the front face 100 such that in a closed state the tubing set 3 is held on the infusion device 1.

From the pump module 32 tube sections 320, 321 extend. Of these tube sections 320, 321, an upstream tube section 321 connects the pump module 32 to a container containing a medical fluid, whereas a downstream pump section 320 connects the pump module 32 to a patient B for delivering the medical fluid towards the patient B. The infusion device 1 comprises a pump mechanism 11 (illustrated only schematically in FIG. 3) having for example a wobbling device acting onto the pump module 32 for peristaltically pumping a medical fluid through the tubing set 3 towards the patient B.

The invention may be implemented in the infusion device 1 according to FIG. 3 in an analogous fashion as described above, such that it shall be referred to the above. In the storage device 16 a compliance value of the tubing set 3 may be stored, wherein different compliance values for different tubing sets 3 of different types and of different manufacturers may be stored. The processor device 15 controls the operation of the infusion device 1 and, from the readings of a force sensor 14 measuring a force on the downstream tube section 320, the pressure P in the downstream tube section 320 may be determined and may be observed in order to detect an occlusion O in the system.

The invention is not limited to the embodiments described above, but can be carried out in an entirely different fashion. In particular, the invention generally is applicable to different kinds of infusion devices used for different purposes for administering a medical fluid into a patient.

LIST OF REFERENCE NUMERALS

1 Infusion device
10 Housing
100 Front face
101 Receptacle
102 Channel
103 Housing element (door)
11 Pumping mechanism
12 Receptacle
13 Display device
14 Force sensor
15 Processor device
16 Storage device
2 Pumping device (syringe)
20 Cylindrical tube
21 Plunger
210 Head
3 Delivery line
30, 31 End
32 Pump module
320, 321 Tube section
A Actuation direction
B Patient
D Pivoting axis
O Occlusion
P Pressure
$P_{thres}$ Pressure threshold
t time
T Duration

The invention claimed is:

1. An infusion device for administering a medical fluid to a patient, comprising:

a pumping mechanism for pumping a medical fluid from a fluid container through a delivery line towards a patient at a set flow rate, a sensor device for measuring a force on the pumping mechanism or the delivery line, a processor means for deriving, from the force measured by the sensor device, a pressure value indicative of a pressure in the delivery line, the processor means for comparing the pressure value to a threshold value from a user for determining whether an occlusion in the delivery line is present, and a storage means for storing a compliance value associated with the pumping mechanism and/or the delivery line, the processor means for computing, from the compliance value, the flow rate and the threshold value, a dynamic estimate of a duration between a time of an occurrence of an occlusion in the delivery line and a time at which the pressure value exceeds the threshold value, the storage means for storing a multiplicity of compliance values including the compliance value, the multiplicity of compliance values associated with a multiplicity of different pumping mechanisms and/or delivery lines, and wherein if the pumping mechanism comprises a syringe pump, the compliance value is associated with a syringe used on the syringe pump, the fluid container comprising the syringe, and if the pumping mechanism comprises a volumetric pump, the compliance value is associated with a tubing set used on the volumetric pump, the delivery line comprising the tubing set, the processor means for (i) issuing a warning if the dynamic estimate of the duration exceeds a predetermined limit, (ii) preventing the user from entering the threshold value that led to the dynamic estimate of the duration that exceeded the predetermined limit, (iii) prompting the user to enter another, smaller threshold value, (iv) receiving from the user the another, smaller threshold value, and (v) computing, from the compliance value, the flow rate, and the another, smaller threshold value the dynamic estimate of the duration between the time of the occurrence of the occlusion in the delivery line and the time at which the pressure value exceeds the threshold valve, and repeating (i) to (iv), if necessary.

2. The infusion device according to claim 1, further comprising an input device allowing a user to program the flow rate and/or the threshold value.

3. The infusion device according to claim 1, the processor means for computing the dynamic estimate of the duration according to the following equation:

$$T = \frac{P_{thres} \cdot C}{f}$$

wherein

T represents the duration between the time of occurrence of the occlusion in the delivery line and the time at which the pressure value exceeds the threshold value, $P_{thres}$ represents the threshold value, C represents the compliance value, and f represents the flow rate.

4. The infusion device according to claim 1, further comprising a display device configured to display the dynamic estimate of the duration.

5. The infusion device according to claim 1, the processor means for computing the threshold value such that the dynamic estimate of the duration is required to fall into a predefined range.

6. A method using an infusion device for administering a medical fluid to a patient, in which:

a pumping mechanism pumps the medical fluid from a fluid container through a delivery line towards the patient at a flow rate, a sensor device measures a force on the pumping mechanism or the delivery line, a processor means derives, from the force measured by the sensor device, a pressure value indicative of a pressure in the delivery line, wherein the processor means is configured to compare the pressure value to a threshold value from a user for determining whether an occlusion in the delivery line is present, and a storage means, the method comprising:

storing on the storage means a compliance value associated with the pumping mechanism and/or the delivery line, computing using the processor means, from the compliance value stored on the storage means, the flow rate and the threshold value, a dynamic estimate of a duration between a time of an occurrence of an occlusion in the delivery line and a time at which the pressure value exceeds the threshold value, wherein the storage means stores a multiplicity of compliance values including the compliance value, the multiplicity of compliance values associated with a multiplicity of different pumping mechanisms and/or delivery lines, wherein if the pumping mechanism comprises a syringe pump, the compliance value is associated with a syringe used on the syringe pump, the fluid container comprising the syringe, and if the pumping mechanism comprises a volumetric pump, the compliance value is associated with a tubing set used on the volumetric pump, the delivery line comprising the tubing set, and using the processor means, (i) issuing a warning if the dynamic estimate of the duration exceeds a predetermined limit, (ii) preventing the user from entering the threshold value that led to the dynamic estimate of the duration that exceeded the predetermined limit, (iii) prompting the user to enter another, smaller threshold value, (iv) receiving from the user the another, smaller threshold value, and (v) computing, from the compliance value, the flow rate, and the another, smaller threshold value the dynamic estimate of the duration between the time of the occurrence of the occlusion in the delivery line and the time at which the pressure value exceeds the threshold valve, and repeating (i) to (iv), if necessary.

7. The method according to claim 6, wherein computing the dynamic estimate of the duration is performed according to the following equation:

$$T = \frac{P_{thres} \cdot C}{f}$$

wherein

T represents the duration between the time of occurrence of the occlusion in the delivery line and the time at which the pressure value exceeds the threshold value, $P_{thres}$ represents the threshold value, C represents the compliance value, and
f represents the flow rate.

8. The method according to claim 6, further comprising displaying the dynamic estimate of the duration.

9. The method according to claim 6, further comprising, using the processor means, computing the threshold value such that the dynamic estimate of the duration is required to fall into a predefined range.

\* \* \* \* \*